US012685503B2

(12) United States Patent
Baer-Beck

(10) Patent No.: US 12,685,503 B2
(45) Date of Patent: Jul. 21, 2026

(54) METHOD FOR ESTABLISHING COMPENSATION INFORMATION TO COMPENSATE FOR A BENDING OF A COUCH IN COMPUTED TOMOGRAPHY, COMPUTED TOMOGRAPHY FACILITY, COMPUTER PROGRAM AND ELECTRONICALLY READABLE DATA MEDIUM

(71) Applicant: Siemens Healthcare GmbH, Erlangen (DE)

(72) Inventor: Matthias Baer-Beck, Spardorf (DE)

(73) Assignee: Siemens Healthineers AG, Forchheim (DE)

( * ) Notice: Subject to any disclaimer, the term of this patent is extended or adjusted under 35 U.S.C. 154(b) by 503 days.

(21) Appl. No.: 18/329,068

(22) Filed: Jun. 5, 2023

(65) Prior Publication Data

US 2023/0389886 A1     Dec. 7, 2023

(30) Foreign Application Priority Data

Jun. 7, 2022    (EP) ..................................... 22177562

(51) Int. Cl.
*A61B 6/00*         (2024.01)
*A61B 6/03*         (2006.01)
        (Continued)

(52) U.S. Cl.
CPC ............ *A61B 6/5276* (2013.01); *A61B 6/032* (2013.01); *A61B 6/0407* (2013.01);
        (Continued)

(58) Field of Classification Search
CPC ...... A61B 6/5276; A61B 6/0407; A61B 6/547
See application file for complete search history.

(56) References Cited

U.S. PATENT DOCUMENTS 4,233,507 A     11/1980  Volz
2002/0186819 A1   12/2002  Proksa
        (Continued)

FOREIGN PATENT DOCUMENTS

DE           60109806 T2      3/2006
DE        102014210458 A1    12/2015

OTHER PUBLICATIONS

Lagarias J.C. et al.:"Convergence Properties of the Nelder-Mead Simplex Method in Low Dimensions." SIAM Journal of Optimization. vol. 9, No. 1, 1998, pp. 112-147.

*Primary Examiner* — Dani Fox

(74) *Attorney, Agent, or Firm* — Harness, Dickey & Pierce, P.L.C.

(57)             ABSTRACT

One or more example embodiments provides a method for establishing compensation information to compensate for a bending of a couch of an object table, in particular patient table, of a computed tomography facility under the weight of an object to be recorded, in particular of a patient, wherein a target region image dataset of a target region of the examination object is recorded with the computed tomography facility at a recording position of the couch, wherein at least one marker visible in x-ray imaging is provided on or in the couch and a three-dimensional reference dataset of the marker is provided for a non-loaded couch, wherein the compensation information is established from a comparison between the reference dataset and the target region image dataset.

20 Claims, 4 Drawing Sheets

(51) Int. Cl.
       *A61B 6/04*          (2006.01)
       *G06T 7/73*          (2017.01)
(52) U.S. Cl.
       CPC ............ *A61B 6/0492* (2013.01); *A61B 6/547*
                     (2013.01); *G06T 7/74* (2017.01); *G06T*
                *2207/10081* (2013.01); *G06T 2207/20081*
                     (2013.01); *G06T 2207/30004* (2013.01)

(56)                    References Cited

U.S. PATENT DOCUMENTS

| | | | |
|---|---|---|---|
| 2008/0031414 A1 | 2/2008 | Coppens et al. | |
| 2008/0123924 A1* | 5/2008 | Nabatame ............ | A61B 6/0487 |
| | | | 382/131 |
| 2015/0343237 A1 | 12/2015 | Hausotte et al. | |
| 2021/0090291 A1* | 3/2021 | Stahl ................... | A61B 6/0492 |

* cited by examiner

METHOD FOR ESTABLISHING COMPENSATION INFORMATION TO COMPENSATE FOR A BENDING OF A COUCH IN COMPUTED TOMOGRAPHY, COMPUTED TOMOGRAPHY FACILITY, COMPUTER PROGRAM AND ELECTRONICALLY READABLE DATA MEDIUM

CROSS-REFERENCE TO RELATED APPLICATION(S)

The present application claims priority under 35 U.S.C. § 119 to European Patent Application No. 22177562.0, filed Jun. 7, 2022, the entire contents of which are incorporated herein by reference.

FIELD

One or more example embodiments of the present invention relates to a method for establishing compensation information to compensate for a bending of a couch of an object table, in particular a patient table of a computed tomography facility, under the weight of an object to be recorded, in particular of a patient, wherein a target region image dataset of a target region of the examination object is recorded with the computed tomography facility at a recording position of the couch. Moreover, the invention relates to a computed tomography facility, to a computer program and to an electronically readable data medium.

RELATED ART

Interventions, in particular in the medical field, are frequently undertaken after prior recording of images in order to identify and/or to localize a target region of the intervention. This is in particular sensible when minimally invasive interventions and/or radiation treatment/radiation therapy are to be carried out, since here the target region is to be found as accurately as possible without any direct line of sight. If computed tomography is used as the imaging modality for the intervention imaging, although the object, in particular the patient, remains positioned on the same couch of the same object table, in particular patient table, it is however in most cases necessary for the recording position of a target region image dataset for localization of the target region of the intervention to differ from the intervention position at which the intervention will subsequently be carried out, since work for intervention cannot expediently take place within the gantry or in general within a patient opening of the computed tomography facility.

Computed tomography facilities, which can also be employed for interventions, usually have an object table, in particular patient table, which comprises a carrier structure, for example at least a table foot, on which the couch, for example a patient couch, is movably supported in at least one direction, in particular a z direction. Since the carrier structure, by its nature, is located outside the gantry, to record an image the couch is moved from a start position, in which the object is positioned above the carrier structure for example, in such a way that the recording position is reached, at which the target region of the object is to be found within the gantry and thus within the field of view of the computed tomography facility. Since the couch with the object positioned thereon projects in a cantilevered manner into the object opening, in particular patient opening, of the gantry, because of the force of gravity and the high additional mass of the object, this can result in a bending of the couch from the horizontal under the weight of the object.

If planning is then carried out on the target region image dataset, in which for example positions to be treated or generally the target region or locations related to this are localized, the height of the target region in the recording position can correspondingly deviate from the height of the target region at the intervention position, since another, in particular no, relevant bending of the couch at all occurs during positioning of the target region above the carrier structure.

To put it differently, in computed tomography interventions usually first of all, in a planning scan, a recording of a target region image dataset of the object takes place, after which the intervention, for example a needle path for a biopsy, is planned based on the target region image dataset, in particular thus the images reconstructed from the planning scan. Because of the nature of the computed tomography the planning scan is undertaken with the object within the gantry of the computed tomography facility, wherein however the intervention, for example the biopsy, takes place outside the gantry of the computed tomography facility. There is thus a discrepancy in the geometrical setting between the image recording in the middle of the gantry and the intervention position where the intervention is carried out. Through the bending of the couch in the vertical direction occurring as a result of the weight of the object, intervention image data is recorded at the recording position that is located at a lower position than the actual position of the target region during the intervention.

If for example external guidance facilities or localization facilities, for example laser-based guidance facilities, are used in order to assist the person carrying out the intervention during the intervention, for example by visualization of a needle path, a geometrical error between the target region image dataset and the real object position occurs during the intervention auf, so that the intervention might not be able to be carried out optimally, since the accuracy of the visualization by the guidance facility is based on the assumption that the geometrical relationships and characteristics do not differ between the planning scan at the recording position and the actual intervention at the intervention position.

Another example of these types of non-invasive interventions is a radiation treatment, in particular radiation therapy, in a target region of the object, where for example, on the basis of the planning scan, the treatment position, for example a tumor as target region, can be localized. The localization information of the target region is then usually related to reference positions on the surface of the object, for example on the skin of the patient. The reference positions are marked in the target region image dataset and transmitted to the real object via a for example laser-based guidance facility by visualization, so that so-called reference markers can be provided on the surface of the object, for example the skin of the patient, which can be visualized by lasers for example.

It is also the case for radiation treatment that the guidance facility operates outside the gantry, for example is attached to a front cover of the gantry, so that the visualization takes place outside the gantry. Thus there is also planning and visualization in different positions here. The difference in the bending of the couch is then translated directly into an error in respect of the positioning of reference markers, which can reduce the quality of the radiation treatment.

In this context it has already been proposed in the prior art with regard to radiation treatment that a look-up table for the planning phase be provided, which is part of the documentation of the system and shows the bending of the couch at various positions. Then, based on the look-up table, the user must manually correct the target region image dataset or results resulting therefrom, which can lead to imprecisions.

For guidance during a minimally invasive intervention as intervention a computational correction procedure has already been proposed. In this the assumption is made that the bending of the couch of the object table can be described by a function DT(c, x), wherein x are the input parameters of the function, for example parameters on which the bending of the table depends, and c is a vector of open coefficients, which for computation of the bending of the table must be calibrated on the basis of known input parameters x. In this case for example the assumption can be made that the bending of the table depends on the load on the table, the relative position of the load on the table in the longitudinal direction (z direction) and the current position of the table in the longitudinal direction, for example relative to a rest position of the table. Naturally further parameters are also conceivable, for example the alignment of the object, for a patient for example feet first/head first, the couch direction, a model of the object table and the like.

The open coefficients c of the function DT must be calibrated beforehand, wherein the calibration is carried out by measurements of the bending of the table while using a defined and known load on the couch. The open coefficients c are then adjusted so that the function DT specifies the measured bending of the couch. For example, the coefficients can be computed by minimizing the quadratic distance between the measured bending of the couch and the function DT, wherein a polynomial can be employed as the function DT for example.

In this procedure of the prior art calibration measurements are usually carried out for the bending of the couch on a reference system, i.e. in a comparable computed tomography facility. The calibration measurements are extremely time-consuming and complex. Another thing is that the corresponding function DT established is not specific to a particular computed tomography facility but is calibrated as a result of the characteristics of the reference system. Differences between the reference system and the system actually given can negatively affect the quality of the estimation of the bending of the couch and the correction.

This also leads in particular to new calibration measurements always having to be carried out when a new object table, in particular a new model or a new type, is introduced or when the mechanical characteristics of a given type of object table change. This means that there is high outlay in time during the development cycle. Calibration measurements must moreover be carried out separately for different configurations of the object table. For example, the use of an additional plate for placing on the couch, which has specific characteristics suitable for the intervention and/or suitable in other ways, is known in the prior art. Such additional plates are frequently also referred to as "overlays". Thus it is known for example for radiation therapy that stiffer carbon plates are placed on the couch, which naturally also has an influence on the bending. Then the calibration measurements for the function DT, which delivers compensation information for compensating for the height difference, i.e. the bending of the couch, must be carried out separately for each combination of available object tables and additional plates. This is problematic in particular when for example overlays from third-party providers can be used.

A further disadvantage of this approach is that calibration coefficients must be provided and stored for each combination of object table and additional plate/overlay.

It can also be useful with other procedures to carry out such a compensation, for example, when a process position different from a recording position of the target region image dataset is a further recording position in which an additional image dataset is recorded, the image contents of which are to be connected spatially to the target region, in which then however another bending of the couch is present. Therefore the term process or process position in the present case may not just relate to corresponding intervention positions but also to application cases extending beyond this.

SUMMARY

One or more example embodiments of the present invention provide an easily implementable and more accurate correction possibility through compensation information for bendings of the couch that are different in particular between a recording position and a process position.

To achieve this object, in accordance with the invention a method with the features of claim 1, an x-ray facility with the features of claim 13, a computer program with the features of claim 14 and an electronically readable data medium with the features of claim 15 are provided. Advantageous embodiments emerge from the subclaims.

BRIEF DESCRIPTION OF THE DRAWINGS

Further advantages and details emerge from the exemplary embodiments described below and also with the aid of the drawings. In the drawings.

DETAILED DESCRIPTION

Figure 1:
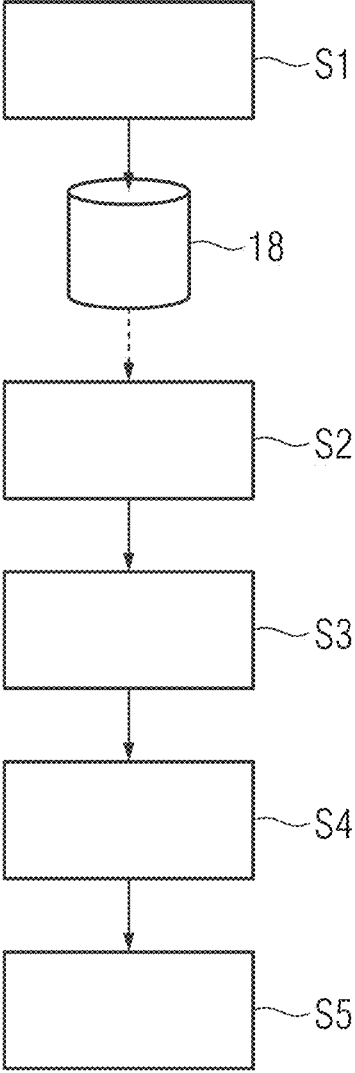
FIG. 1 shows a flow diagram of an exemplary embodiment of the inventive method.

In a method of the type stated at the outset there is provision in accordance with one or more example embodiments of the present invention for at least one marker visible in x-ray imaging to be provided on or in the couch and for a three-dimensional reference dataset of the markers for a non-loaded couch to be provided, wherein the compensation information is established from a comparison between the reference dataset and the target region image dataset.

In general terms one or more example embodiments of the present invention thus allows a measurement of the bending of the couch by comparison with a reference dataset, in which the bending of the couch by the object is not present. The basis for the comparison is formed by markers able to be localized both in the reference dataset and also in the target region image dataset. The target region image dataset can in this case in particular serve to establish localization information of the target region, which can be the subject of the compensation.

The present invention can also be based, in advantageous application cases, on a situation in which a process related to a target region of an object, in particular an intervention in the target region of the object, for example of a patient, is to be carried out at a process position. To this end target region image data is recorded in a planning scan first of all at the recording position different from the process position at which recording position the target region is located in the field of view of the computed tomography facility, in particular thus in an object opening of the gantry, said target region image data is then to be evaluated in order to provide localization information related to the target region, which is to be used at the process position, in particular intervention position. In concrete terms in the example of a medical intervention, the patient is moved before the intervention i.e. with the target region into the gantry and the target region image dataset is recorded at the corresponding recording position. Then the patient is brought into the intervention position (as process position), and after conclusion of the planning the intervention can be carried out based on the localization information. Here however, due to a bending of the couch in the recording position caused by the weight of the object to be recorded, the result can be deviations in height between the target region in the target region image dataset and the real target region at the process position, which is why the present invention establishes compensation information, which describes precisely this deviation in height occurring though the bending of the couch and is to be used for correction. In this case the compensation information, which will be described in greater detail, which describes the bending of the couch, thus specifies a value of a relative height by which the target region image dataset or the localization information is to be shifted in order to obtain more accurate knowledge about the location of the target region at the process position and to be able to carry out the intervention with high precision and quality.

To put it another way there can be provision for the compensation information to be used for compensation of localization information of the target region to be used in the process, in particular to be displayed and/or to be aimed toward, established from the target region image dataset in the process position and/or for height compensation of the target region image dataset itself. The localization information corrected via the compensation information or derived from the corrected target region image dataset can be used for example for controlling a guidance facility, in particular a laser-based guidance facility for visualization of positions related to the target region and/or of a display facility comprising a monitor for in particular real time display of a position of an in particular medical intervention instrument based on position data of the intervention instrument.

In general, within the framework of the present invention there can be provision for the couch to be supported movably on a carrier structure of the object table, in particular linearly and/or between the process position and the recording position, wherein naturally end positions of the movability extending beyond the process position and the recording position can be provided. In this case the object, in particular the target region, is located in the process position, preferably at least essentially above the carrier structure, so that no appreciable bending of the couch occurs there.

In this case it should also be pointed out at this juncture that a certain, far smaller bending under the inherent weight of the couch can occur, which can be ignored however for the application cases discussed here. In particular, the bending of the couch by the weight of the object is greater by at least an order of magnitude than the bending of the couch as a result of the inherent weight of the couch. For example, object tables are known in which, with a load on the couch, a bending of the couch, thus a difference in height, in recording positions in the range of 6 to 20 mm can occur, while the bending under their own weight would merely amount to 0.3 to 0.6 mm.

In order to overcome the problems of the prior art, in particular the necessity for calibration measurements and the lack of compensation specific to a computed tomography facility, in accordance with one or more example embodiments of the present invention a procedure based on at least one marker for measuring the bending of the couch is proposed. In this case at least one marker, in particular a number of markers, is integrated into the couch of the object table or connected in a fixed position to the couch. The markers are visible in x-ray images, so that this also applies to the target region image dataset to be recorded in any event. If it is now known from a reference dataset suitable for a comparison, which is actually provided in accordance with one or more example embodiments of the present invention, where the markers are to be located in the target region image data, the deviation that occurs through the bending of the couch under the weight of the object, and thus the compensation information, can be established by a corresponding comparison.

By comparison with the known approaches of the prior art, no complex calibration measurements are needed, but only a single reference dataset containing information about the marker position without bending by an object, which reference dataset in particular can be specific to a particular computed tomography facility or table configuration, is sufficient. For example the reference dataset can be established in a reference measurement during the installation of the computed tomography facility or within the framework of an initial commissioning, wherein there can be a simple uncomplicated repetition which does not last long by the operator himself or by a service engineer when changes are made to the computed tomography facility, which relate to the object table, in particular to its couch. In another example, it is also conceivable to derive the reference dataset from the known construction of the object table and in particular of the couch. In each case there is no need to store calibration data and tables for different combinations of object tables and additional plates, in particular overlays. In other words it can also be said that with a couch able to be provided with an additional plate, in particular exchangeable overlays, the same reference dataset can be provided for all additional plates. This is because it is ultimately irrelevant whether the couch becomes stiffer through the additional plate or the object is supported higher by this, since reference is only made to a reference in which a bending by the weight of the object does not occur.

As already mentioned, an especially advantageous embodiment of the present invention can make provision for the reference dataset to be established in a reference measurement, in particular carried out during an initial commissioning of the computed tomography facility with current couch characteristics with a non-loaded couch. Thus the proposed method can begin with a reference measurement, for which no patient or other object is located on the couch, so that the reference measurement, which is carried out like a usual computed tomography scan with the computed tomography facility, merely contains image data from the at least one marker and the table itself, in particular of the couch. Reference images can be reconstructed from the results of the reference measurement via usual reconstruction methods, in which then merely the at least one marker and the couch are visible. These reference images, which can be reconstructed from the project images recorded in the reference measurement via back projection, for example, can form the reference dataset or be further processed to establish it. The reference measurement only has to be carried out once with respect to a specific couch configuration. It should be noted that for a change in the couch characteristics, for example with a replacement of the couch or of the object table as a whole, a new reference measurement can be carried out.

In an especially advantageous embodiment of the invention, there can be provision for a reference height setting to be selected for the reference measurement of the couch which can be adjusted in terms of its height, so that the at least one marker is acquired in each projection image of the reference measurement, wherein with a deviation in the height setting from the reference height setting the reference dataset for establishing the compensation information is shifted in the height direction by this deviation. In order to obtain an image of the at least one marker that is as accurate as possible, the couch should be positioned in the field of view of the computed tomography facility so that the at least one marker is ideally visible in all projection images that are recorded in the reference measurement. With a height-adjustable couch, wherein in particular corresponding height adjustment means can be provided in the carrier structure, a relatively high position can thus expediently be chosen as the reference height setting, for example the couch can be positioned where otherwise the object, in particular its target region, would be arranged. Since the object table is generally registered with the coordinate system of the computed tomography facility, it is naturally possible without any problems to calculate back to other height settings, for example those in which then the target region instead of the couch is positioned centrally in the field of view of the computed tomography facility. The reference dataset merely has to be shifted from the reference height setting by the deviation from the current height.

In this context it should also be noted at this point for the sake of completeness that in general naturally the current position is known as a result of corresponding setting means/adjustment means of the patient table, in particular also in the direction of movement, in which in particular a switch is made between the process position and the recording position, wherein the direction of movement generally preferably corresponds to the longitudinal direction of the couch and/or which in particular is parallel to the axis of rotation of an x-ray source or to the entire recording arrangement of the computed tomography facility. Corresponding setting means for a linear movement of couches on object tables are already widely known in the prior art and do not have to be shown in detail here. For example, the object table can have a control unit, which provides the current setting of the object table to a control facility of the computed tomography facility.

As an alternative and/or during merging of data, there can additionally also be provision within the framework of the present invention for the reference dataset to be provided from construction data of the object table. Ultimately it is already known due to the construction of the object table where the at least one marker is attached within the couch or on the couch, so that from this a three-dimensional dataset can be created, which shows this position in the non-loaded state in the three-dimensional space. A comparison with x-ray data of the target region image dataset is still possible however, since it is also known from the construction data which characteristics the different materials of the object table, but in particular of the at least marker, have. Since also in the recording of target region image datasets usable x-ray spectra of the computed tomography facility are known, it is possible also to provide reference data comparable with x-ray data from construction data.

In a development of one or more example embodiments of the present invention there can be provision for at least one elongated, in particular wire-like marker element extending in a direction of movement of the couch which is in particular parallel to an axis of rotation of an x-ray source of the computed tomography facility and/or corresponds to a longitudinal direction of the couch, in particular between the recording position and the process position, to be used as the marker. It can be expedient here for the marker element to extend at least essentially over all sections of the couch able to be positioned in the field of view of the computed tomography facility or even at least essentially over the entire length of the couch. In this way it is ensured that in all conceivable recording positions a recording of the at least one marker element is actually also conceivable. The parallelism with respect to the direction of movement between the process position and the recording position, which usually corresponds to the longitudinal direction of the couch (z direction), ensures that, regardless of the recording position actually chosen, the same image of the at least one marker element is produced for all recording positions, so that the comparison is able to be carried out highly accurately. The marker elements can be given by thin wires, for example, which are preferably integrated into the couch, for example are molded into it. However, in other cases it can also be expedient to integrate the at least one marker or the marker element within the couch, since then the marker element is especially protected from changes in position and orientation or damage. As well as the option, for example of primary shaping the plate of the couch by the at least one marker element, other possibilities for integration are naturally also conceivable, for example the provision of grooves in the couch able to be closed off and the like. As an alternative or in addition, an attachment of at least one of the at least one marker element to the couch is naturally also conceivable, for example by corresponding attachment means on the surface or in recesses provided correspondingly for this.

In this case it is especially expedient, since the comparison is facilitated by this, to use a number of markers and thus also marker elements, or to select marker elements of a cross section at right angles to the longitudinal direction, which offers advantages in respect of the orientation, for example. In this case it should be noted at this point that the at least one marker element does not absolutely have to be suited to a complete three-dimensional orientation determination, since it is a matter of determining a height location as accurately as possible, for which markers of the same type also arranged in one plane may already be extremely useful.

An expedient development of one or more example embodiments of the present invention can make provision for at least three parallel marker elements to be used, in particular one in the middle and two, preferably symmetrically, adjacent to it, preferably in edge areas of the couch, and/or at different heights within the couch. It is thus possible to employ wire-type marker elements for example, of which one is arranged in the middle, one on the left and one on the right with regard to the cross section of the couch, wherein the outer marker elements can preferably be provided on the left and the right edge of the couch.

The at least one, in particular cylindrical, marker element can for example have a diameter of 1 to 20 mm and/or preferably be made of plastic. In general terms materials with an x-ray attenuation in the range of −750 to 100 HU (Hounsfield Units) are especially suitable. Such materials are sufficiently clearly recognizable in the image data in a reference measurement or a planning scan, but do not attenuate the x-ray radiation too greatly, so that the occurrence of artifacts, as is known for example from metals, is avoided as much as possible. Thus quite weakly attenuating materials, in particular suitable plastics such as ABS (Acrylonitrile Butadiene Styrene Copolymers) can be employed.

The reference dataset can preferably be established showing just the at least one marker. In the case of a reference measurement it is possible in this connection for example to segment the at least one marker, in particular with additional use of construction data, whereby all other regions of the image are filled with the attenuation value, in particular HU value, for air, thus −1000 HU. In this way an easy to manage reference dataset is produced, to which comparisons with the relevant image contents, in particular markers embodied as marker elements, can be concentrated and other, rather complex structures do not have to be considered for simple and effortless establishment of the compensation information. Particular advantages are produced when, which is preferred in any event within the framework of the present invention, the comparison takes place in the projection space, since forward projections for establishing corresponding comparison images from the reference dataset are then able to be computed easily and robustly, and the comparison, in particular a correlation, is also able to be carried out easily and with less effort but still robustly.

In an especially advantageous embodiment of the present invention there can be provision that, for comparing the reference dataset with the target region image dataset, at least one comparison image with a recording geometry of an assigned projection image of the target region image dataset is established by forward projection from the reference dataset and is compared with the assigned projection image, in particular for a number of, preferably all, projection images of the target region image dataset showing at least one of the at least one marker. In other words, for establishing the bending of the couch for a given target region image dataset, a simulated forward projection of the at least one marker from the reference dataset is undertaken using the recording geometries of the actual planning scan, wherein the comparison is then carried out in the projection space with corresponding projection data of the planning scan. In this case it was recognized that in the recording of the target region image dataset usually the target region of the object is placed in the center of the field of view of the computed tomography facility, so that this can be detected in all projection images, in particular from all projection angles used. This may however lead to the at least one marker only being able to be seen in one part of these projection images, so that during an attempt at reconstruction of the at least one marker in the image space from the projection images, errors and/or local artifacts, which may hamper the comparison in the image space, may occur as result of missing data. To put it another way, due to the extremely low vertical position of the couch, it can occur for processes, in particular interventional applications, that at least a part of the couch is not always able to be located in the field of view of the computed tomography facility, so that on application of this marker-based approach, there can be problems in the image space of the attenuation values. Through the application in the projection domains, as proposed here, this restriction is overcome, since the at least one marker is at least partly visible in the projection data, in particular rather in the anterior-posterior projection images or posterior-anterior projection images.

Here the comparison can be made for recorded projection images comprising a number of rows row-by-row and/or after a conversion into a parallel beam geometry. It is especially preferred however when a common comparison, for example the establishment of a common correlation value, is carried out for different recording geometries, by for example the projection images being formulated as at least one projection dataset which contains projection data for different projection angles and/or image coordinates.

In this context an especially expedient development is produced when the comparison images and the projection images are highpass-filtered before the comparison using the same filter. The highpass filtering can then relate in particular to at least one dimension at right angles to the direction of extent of the elongated, at least one marker element, through which in particular the at least one marker is sufficiently clearly highlighted in the projection images of the target region image dataset. In concrete terms provision can be made for a two-dimensional Gaussian lowpass filter to be applied for highpass filtering and the result is subtracted from the respective unfiltered image.

Less preferred, but basically conceivable, it is also possible, as an alternative or in addition, for the comparison to be made in the image space of a reconstruction image of the target region image dataset reconstructed from the projection images of the target region image dataset, in particular for at least one of the at least one marker, which is visible in each projection image of the target region image dataset used for reconstruction of the reconstruction image. Since the preferred said last condition is not able to be ensured in many cases, as explained, in general working in the projection space is preferred.

In a preferred embodiment of the invention, in a concrete approach for establishing the compensation information, there can be provision for comparison images to be established for different relative heights of the at least one marker from the reference dataset, while taking into account the recording geometry for the target region image dataset, wherein an optimized relative height with a highest match between the at least one corresponding comparison image and at least one corresponding target region image of the target region image dataset is determined as compensation information. As has already been discussed, the reference dataset is actually registered with the coordinate system of the computed tomography facility. It defines a reference height related to a state of the couch not loaded by an object, which where necessary is adapted in relation to a deviation of the height setting, as discussed. The reference height of the marker thus corresponds to the assumption that no bending of the couch by an object located thereon is present at the height setting currently used. The deviation from this reference height is the deviation in height to be compensated for, in other words the relative height, wherein different possible deviations in heights can be selected by shifting the reference dataset in the coordinate system of the computed tomography facility or by shifting the recording geometry in the coordinate system of the computed tomography facility. It is proposed here that an optimization algorithm be employed in order to establish the relative height, i.e. the deviation in height from the reference height, for which the highest match between the at least one comparison image for this relative height and the target region image dataset is given. The optimized relative height determined in this way corresponds to the bending of the couch measured by the target region image dataset.

In the preferred exemplary embodiment, in which the system works in the projection space, this means in concrete terms that for each assigned projection image of the target region image dataset, a number of comparison images with different relative heights of the at least one marker are established, wherein the relative height with a highest match between the corresponding at least one comparison image and the assigned at least one projection image is determined as compensation information. In other words, the height of the reference dataset or of the markers described therein and thus of the at least one comparison image is varied, for example during the forward projection from the reference dataset, and the bending of the couch is estimated by the relative height of the markers being found that best match the projection data of the planning scan.

In concrete terms here the optimized relative height can be selected in an optimization algorithm for maximizing the match described in particular by a measure of similarity and/or correlation. Here, to particular advantage, there can be provision, in particular for comparison images to be compared with projection images, for an in particular two-dimensional normalized measure of cross-correlation to be used. Thus the two-dimensional normalized cross-correlation between the projection data of the target region image dataset and the forward projection can be used as a cost function of the optimization algorithm for the optimization of the relative height for example, wherein other measures of image similarity or image correlation can be employed however. The idea behind this approach is the fact that the cross-correlation between the projection data of the target region image dataset and the forward projection of the reference dataset reaches a maximum when the height of the at least one marker in the projection image and the additional comparison image matches.

Since this assumption can be violated by the marker projections being overlaid by features of the object, for example the patient anatomy, as already explained briefly above, for remedying this problem and for general reduction of the influence of the object features, in particular of the patient anatomy, on the cross-correlation, a highpass filter is applied to the projection data of the target region image dataset and also the comparison images of the reference dataset, in particular a two-dimensional highpass filter. Only after this is the measure of similarity and/or correlation determined.

A simplex algorithm can be used as the optimization algorithm for example, wherein the use of other optimization algorithms basically known in the prior art is also conceivable. The simplex algorithm is described for example in an article by Jeffrey C. Lagarias et al., "Convergence Properties of the Neldert-Mead-Simplex Method in Low Dimensions", SIAM J. OPTIM. Vol. 9, No. 1, Pages 112 to 147.

In another approach, it is also conceivable within the framework of the present invention to carry out the comparison so-to-speak implicitly, by a trained function, i.e. in particular an artificial intelligence algorithm, which has been trained by machine learning, being learned accordingly.

In general, a trained function maps cognitive functions that humans associate with other human brains. Through training based on training data (machine learning) the trained function is capable of adapting itself to new circumstances and detecting and extrapolating patterns.

Speaking generally parameters of a trained function can be adapted by training. In particular supervised learning, semi supervised learning, unsupervised learning, reinforcement learning and/or active learning can be used. Above and beyond this representation learning (also known as feature learning) can be employed. The parameters of the trained function can be adapted in particular iteratively by a number of training steps.

A trained function can for example comprise a neural network, a Support Vector Machine (SVM), a decision tree and/or a Bayesian network and/or the trained function can be based on k means clustering, Q learning, genetic algorithms and/or assignment rules. In particular a neural network can be a deep neural network, a Convolutional Neural Network (CNN) or a deep CNN. Over and above this the neural network can be an Adversarial Network, a Deep Adversarial Network and/or a Generative Adversarial Network (GAN).

In this instance, in the present application case, approaches based on deep learning are preferred. In concrete terms there can be provision for example that, to establish the compensation information, a trained function using at least a part of the target region image dataset as input data, on the basis of the reference dataset is used as output data. In this case it is especially expedient if, as training data for the function to be trained, training datasets, which comprise the reference dataset with at least one marker arranged at different relative heights, are created.

Especially advantageously it is also true here that the trained function preferably operates on the projection data of the target region image dataset, thus accepts this as input data. The trained function estimates, generally speaking, the relative height according to the paragraphs described above and thus describes the bending of the couch. The trained function, in particular a CNN, can be trained in this case via the reference dataset for different relative heights as training datasets, in particular while using virtual projection images derived therefrom, so that the trained function translates given projection data as input data into a relative height. The comparison is then made so-to-speak hidden within the neural network or generally the trained function.

As mentioned above, the compensation information can be employed in particular in a method for establishing localization information relating to the target region at a process position provided for a process, in particular an intervention, different from the recording position, in order for example to shift the localization information or target region image dataset already forming the basis for this according to the established bending of the couch, i.e. the relative height. The localization information can then for example be employed for activation of guidance facilities to assist a person carrying out the intervention, for example for visualizing the target region or positions relating to the target region, and/or for activation of process facilities at least partly carrying out the process, such as for example with respect to laser markings/settings for a radiation treatment and/or displays relating to a minimally-invasive instrument and/or for controlling a robot controlling it.

For processes in which the process position is a further recording position for recording an additional image dataset, via one or more example embodiments of the present invention further compensation information for the further recording position of the additional image dataset can be produced, so that the difference between the bendings of the couch established in this way describes the difference in height between image information of the additional image dataset and the target region image dataset.

As well as the method, one or more example embodiments of the present invention also relates to a computed tomography facility for use in processes related to a target region of an object, in particular of a patient, in particular interventions, having an object table, in particular a patient table, with a couch for the object able to be moved in at least one direction, wherein at least one marker visible in x-ray imaging is provided at or in the couch, and a control device, which has:

a storage means, in which a three-dimensional reference dataset of the marker for a non-loaded couch is stored, a recording unit for recording a target region image dataset pointing to the target region of the object at a recording position of the couch, a compensation information establishment unit for establishing compensation information to compensate for a bending of the couch at the recording position under the weight of the object to be recorded, wherein the compensation information establishment unit has a comparison subunit for establishing the compensation information from a comparison of the reference dataset with the target region image dataset, and a compensation facility for compensating for localization information relating to the target region, in particular relating to a process position which differs from the recording position, to be used for the process, in particular to be displayed and/or aimed toward, established from the target region image dataset, due to the compensation information.

Everything stated with regard to the inventive method can be transferred by analogy to the inventive computed tomography facility, so that the advantages already stated can also be obtained with this. In particular the functional units described can be provided by at least one processor of the control facility. The control facility also has as a functional unit in particular a recording unit, which not only can control the recording operation in general, but in particular controls the recording operation for the target region image dataset, in a corresponding embodiment also the recording operation for the reference measurement. In particular a reference dataset establishment subunit of the compensation information establishment unit can thus also be provided, which can evaluate the reference measurement, if necessary while additionally taking account of construction data provided. As a general remark it can also be said that the control facility is embodied for carrying out an inventive method and moreover has components for using the compensation information.

An inventive computer program is for example able to be loaded directly into a storage medium of a control facility of a computed tomography facility and has program means for carrying out the steps of an inventive method when the computer program is executed on the control facility of the computed tomography facility. The computer program can be stored on an inventive electronically readable data medium, which thus comprises control information, which comprises at least one inventive computer program and is embodied in such a way that, when the data medium is used in a control facility of a computed tomography facility, said facility is embodied to carry out an inventive method. This electronically readable data medium can involve a non-transient data medium, in particular a CD-ROM, for example.

Exemplary embodiments of the present invention for an application, here an intervention as a process, in the medical field will be explained in greater detail below. This means that the object there corresponds to a patient, wherein in a target region of the patient, as an intervention for example, a radiation therapy and/or a minimally invasive intervention with a medical instrument (medical intervention instrument) is to take place. The object table in the example below thus involves a patient table. As well as the application cases described here in the medical field, a process, in particular an intervention on other objects, for example in respect of material testing and/or material treatment, is basically conceivable.

FIG. 1 shows an example of a flow diagram of an exemplary embodiment of the inventive method as well as where necessary the steps surrounding it. Before this is discussed in detail, the problem underlying one or more example embodiments of the present invention will first be explained with respect to FIG. 2 and FIG. 3, which each show greatly schematically simplified views of an inventive computed tomography facility 1.

Figure 2:
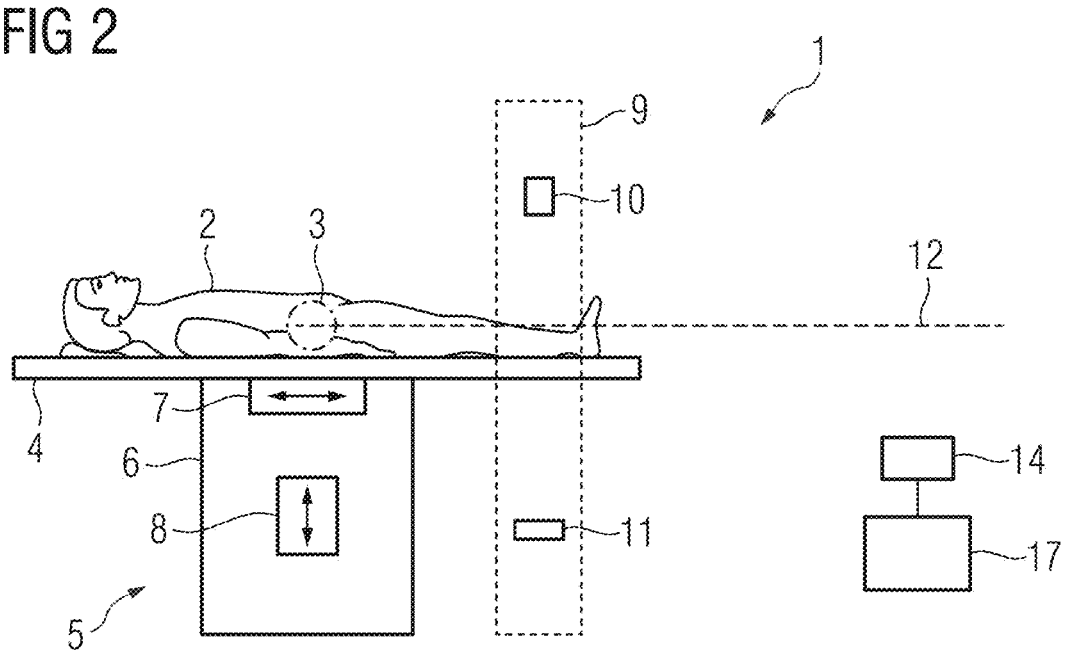
FIG. 2 shows a schematic sketch of an inventive computed tomography facility in a first couch position according to one or more example embodiments.

In the present example, as already mentioned, an intervention in a target region 3, for example at a tumor or another lesion, is to be undertaken on a patient 2 (not belonging to the computed tomography facility 1). To this end the patient 2 is arranged in a specific position and orientation on a couch 4 of a patient table 5, wherein in addition an additional plate not shown here in any greater detail, for example a so-called overlay, can also be provided on the couch 4. In addition to the couch 4 the patient table 5 comprises a carrier structure 6, for example at least one table foot, on which the couch 4 is able to be moved in the longitudinal direction of the couch 4 via corresponding first setting means 7, is able to be adjusted in the height direction via corresponding second setting means 8. The longitudinal direction in this case is parallel to an axis of rotation of a recording arrangement provided in a gantry, only indicated by dashed lines here, said recording arrangement, in the present example, comprising the x-ray source 10 and also an x-ray detector 11. The intervention at the target region 3 cannot be carried out here for a target region 3 located within the gantry in the field of view of the computed tomography facility 1 since access is too restricted. Instead an intervention position of the couch 4 shown in FIG. 2 is used as the process position, in which, in the present example the target region 3 is positioned above the carrier structure 6.

Figure 3:
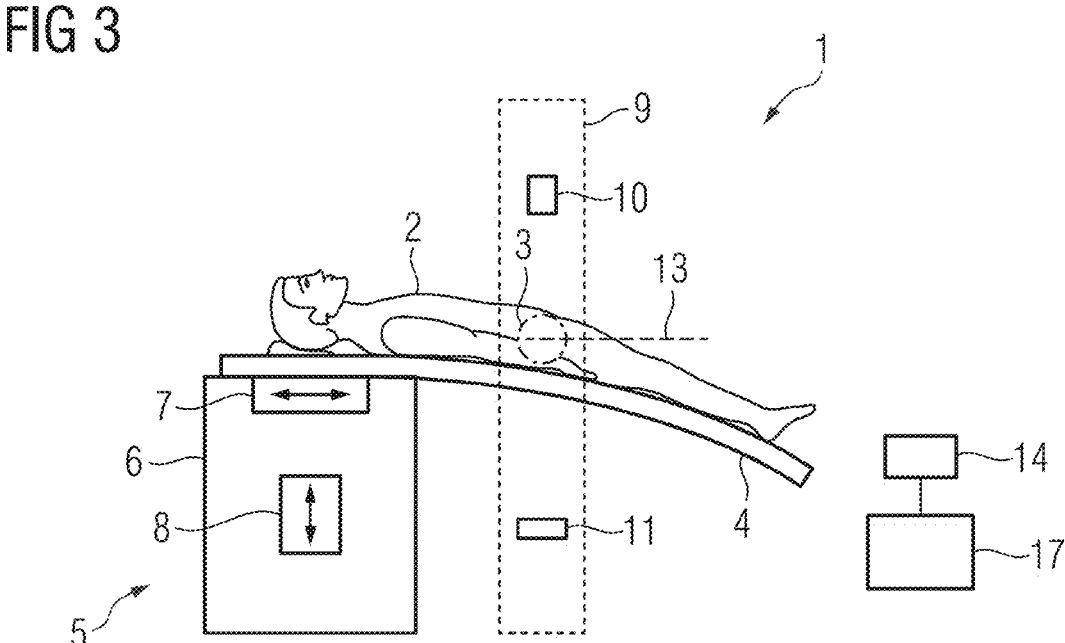
FIG. 3 shows a schematic sketch of an inventive computed tomography facility in a second couch position according to one or more example embodiments.

For planning of the intervention however the recording of a target region image dataset is also to be carried out in a planning scan, for which the couch 4 is to be moved into a recording position indicated schematically in FIG. 3, in which the target region 3 is located in the field of view of the recording arrangement (x-ray source 10, x-ray detector 11) of the computed tomography facility 1, i.e. within the gantry 9, more precisely of an object opening in said facility. Here the couch 4 projects in a cantilevered manner into the object opening of the gantry 9, so that, due to gravity, thus the weight of the patient 2, this results in a slight bending of the couch 4, shown exaggerated in FIG. 3 for presentation purposes. This means that, while the target region 3 is located at a first height 12 in the intervention position shown schematically in FIG. 2, due to the bending of the couch in the recording position shown schematically in FIG. 3 it is located at a second, lower height 13, so that a deviation in height between the target region image dataset and the real position of the target region 3 thus exists in the intervention position.

If now localization information relating to the target region 3 is established by evaluating the target region image dataset without any compensation for this deviation in height due to the bending of the couch, the positions contained therein lie slightly too low. This can lead to imprecisions during the intervention, for example during the visualization of the localization information via a corresponding, in particular laser-based, guidance facility 14.

Therefore there is provision in the exemplary embodiments shown here for establishing the deviation in height through the bending of the couch as compensation information and for providing a corresponding movement of the target region image dataset or of the localization information derived therefrom as compensation.

Figure 4:
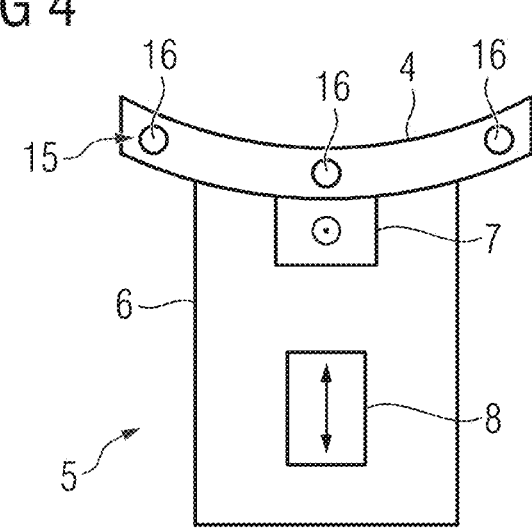
FIG. 4 shows a cross-section through a patient table of the computed tomography facility according to one or more example embodiments.
Figure 5:
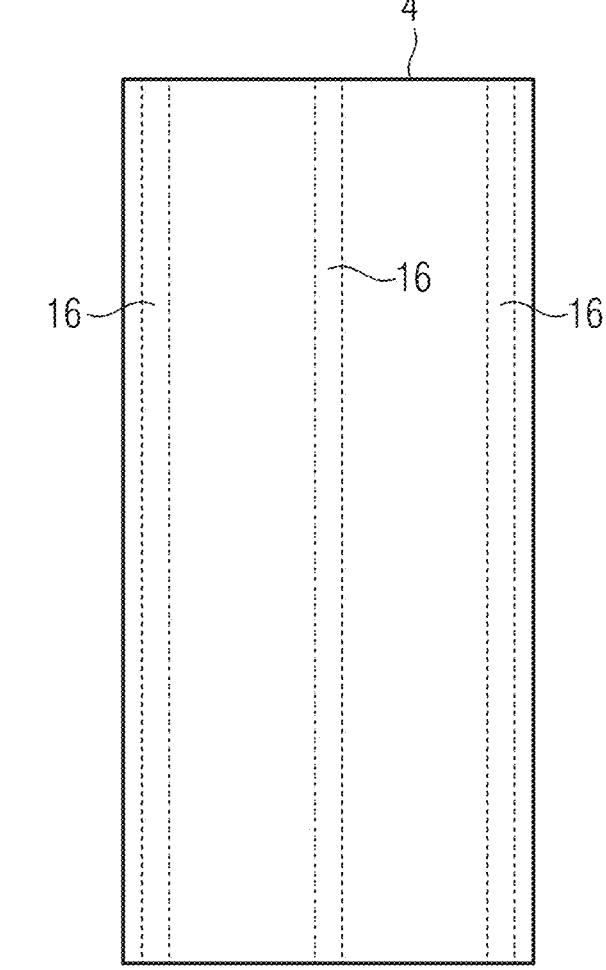
FIG. 5 shows a longitudinal section through a couch of the patient table of FIG. 4 according to one or more example embodiments.

To this end a specific embodiment of the couch 4 of the patient table 5 is first provided in the inventive computed tomography facility 1, as FIGS. 4 and 5 show. Three marker elements 16, which are visible in x-ray imaging, are integrated in or on the couch 4, in the present example integrated into the couch 4, as at least one marker 15. The marker elements 16 in the present exemplary embodiment involve elongated, wire-like plastic cylinders with an HU value in the range of −600 to 100, for example, so that no artifacts that are too strong, resulting in absorption of the x-ray radiation, are produced. The elongated marker elements 16 extend in this case with their longitudinal direction parallel to the longitudinal direction of the couch 4, which actually corresponds to the direction of movement via the setting means 7 between the recording position and the intervention position. Thus the marker elements 16 always look the same, regardless of the actual recording position in the x-ray imaging. In the exemplary embodiment they extend over the entire length of the couch 4, but can also only comprise the area for possible sections of the couch 4 located in recording positions in the field of view. For example, the marker elements 16 can be molded into a couch material of the couch 4 but can also be arranged in a closed groove of the couch 4.

Naturally other concrete embodiments of the marker elements 16 are also conceivable, for example other elongated forms, aligned in parallel to the direction of movement between the intervention position and the recording position and/or other numbers, since three wire-like marker elements 16 are only shown by way of example in this exemplary embodiment, of which one is arranged in the middle, one on the right and the other on the left.

It should also be pointed out that the operation of the computed tomography facility 1 is controlled by a control facility 17, which is also embodied for carrying out the method for establishing the compensation information as well as the further steps now described in greater detail in respect of FIG. 1. The control facility 17 can also comprise a control unit of the patient table 5.

In a step S1 to be carried out just once for each patient table 5 and its arrangement in the computed tomography facility 1 in accordance with FIG. 1, a reference dataset 18 is first established on the basis of a reference measurement. The reference measurement carried out with the recording arrangement in the gantry 9 of the computed tomography facility 1 is in this case a usual computed tomography measurement, it is just that no object is located on the couch 4 and the height setting has been selected via the setting means 8 so that the marker elements 16 are located as at least one marker 15 in the center of the field of view of the computed tomography facility 1, thus the marker elements 16 are to be seen in each projection image of the reference measurement. This makes possible a complete reconstruction of a three-dimensional reconstruction image from the projection images of the reference measurement, which initially shows both the marker elements 16 and also the rest of the table 4. Where necessary with the aid of construction data of the patient table 5, in particular of the couch 4, the marker elements 16 are now segmented. All regions outside the segmented marker elements, for maintaining a reference dataset 18, are then set to the HU value of air, i.e. −1000. The reference dataset 18 in this exemplary embodiment thus merely contains the marker elements 16 as the at least one marker 15. In this regard FIG. 6, by way of example on the left hand side of the figure, shows a sectional diagram 19 from the reference dataset 18, and shows it at right angles to the longitudinal direction/direction of movement of the couch 4, where the elongated marker elements 16 thus in their cross section are also to be seen in the arrangement to be taken from FIG. 4.

The reference dataset 18 is stored in a storage means of the control facility 17, together with the reference height setting of the patient table 5 that was given for this.

If there is now an impending intervention in a target region 3 of a patient 2, the procedure described now can be employed each time on the basis of the same reference dataset 18, in particular even regardless of whether or not an overlay is being used. For this the reference dataset 18 is provided from the storage means and where necessary, with a deviation in the height setting in the recording position from the reference height setting, is shifted in accordance with this deviation, so that the markers 15, here marker elements 16, in the reference dataset 18 are located at the reference height at which they would be arranged if no object were to be located on the couch 4.

The step S2 now initially indicates that the target region image dataset is recorded in the recording position. For this target region image dataset, by using the same, compensation information, which describes the bending of the couch, is now established in a step S3, by ultimately a comparison of the reference dataset 18 with the target region image dataset being carried out for different relative heights, here of course drops, by comparison with the reference height and the relative height, for which the highest match is produced, being determined as compensation information which describes the bending of the couch and also the deviation in height with regard to the target region 3.

Figure 6:
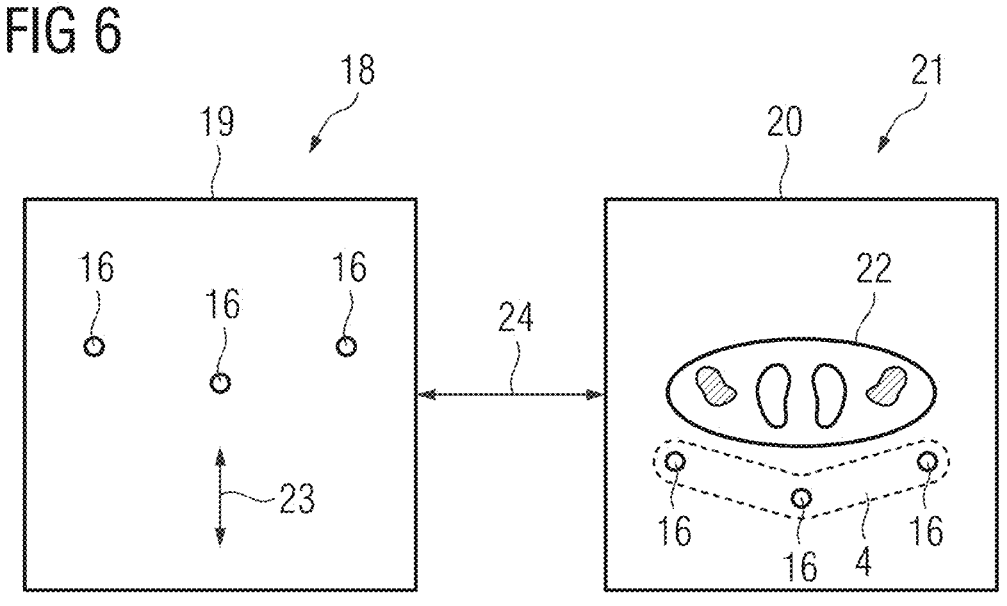
FIG. 6 shows sectional diagrams of a reference dataset and of a target region image dataset according to one or more example embodiments.

This underlying principle is explained in greater detail with respect to FIG. 6, where a corresponding sectional image 20 of the target region image dataset 21 is shown on the right hand side, as well as the sectional image 19 of the reference dataset 18. The target region image dataset 21, as well as the newly visible marker elements 16 also faintly shows the couch 4 as well as anatomy 22 of the patient 2. The relative height is now varied in accordance with the arrow 23, until an optimal match for the comparison symbolized by the arrow 24 is given, wherein the comparison in the present example is not based on sectional images 19, 20, but is preferably carried out in the projection space, i.e. with regard to the projection data. With respect to the variation of the relative height in general, an optimization algorithm is employed in order to determine as compensation information the relative height (optimized relative height) showing the optimal match. This will now all be explained in greater detail with the aid of a concrete exemplary embodiment.

In order to establish the bending of the couch for the given planning scan, i.e. the target region image dataset 21, a simulated forward projection of the reference dataset 18, more precisely of the marker elements 16 contained therein, is firstly carried out while using the recording geometries of the projection images of the actual planning scan. As a result, a set of forward projected comparison images is obtained for each relative height "to be tested", in particular drop in relation to the reference height, of which each is assigned to a projection image of the same recording geometry in the target region image dataset 21. The totality of the projection images of the target region image dataset 21 can in this case be understood as a projection dataset, the totality of the comparison images as a comparison dataset. The projection data is now compared with this comparison data, wherein the height of the markers 15 in the reference dataset 18 is varied during the forward projection and the bending of the table is estimated by finding the relative height of the marker elements 16 of the reference dataset 18 that best match the projection data of the target region image dataset 21. Here an optimization algorithm is employed, the cost function of which comprises a measure of similarity and/or correlation and is thus maximized. In the present concrete form of embodiment, in this case the two-dimensional normalized cross-correlation between the projection data of the target region image dataset 21 and the comparison data of the forward projection of the reference dataset 18 is used, wherein other measures are basically also conceivable.

The assumption that the cross-correlation (or general match) between the projection images and the comparison images reaches a maximum when the height of the marker elements 16 in the assigned projection and comparison images matches can be called into question in that the marker projections in the projection images can be overlaid by the patient anatomy 22. In order to solve this problem and basically reduce the influence of the patient anatomy 22 on the cross-correlation, a two-dimensional highpass filter is applied to the projection images and the comparison images, in concrete terms to the comparison dataset and the projection dataset, before the comparison. In this case a two-dimensional Gaussian lowpass filter can first be applied as a highpass filter for example and the result subtracted from the original data. Naturally other highpass filters can also be employed.

To establish the optimized relative height in this case any numerical optimization algorithm can be employed, wherein in the present example the simplex algorithm is used.

It should also be noted at this point that it would basically also be conceivable to carry out the comparison in the image space, i.e. on reconstructed image data, for example on the basis of sectional images 19, 20, as are shown in FIG. 6. This is less preferred however, since for recording of the target region image dataset 21 the target region 3 is positioned in the center of the field of view of the computed tomography facility 1 and in some projection images the marker elements can therefore not be seen, at least in part, so that a correct reconstruction is at least rendered more difficult and there can therefore be problems during the comparison. This problem can be circumvented by undertaking the comparison in the projection space.

It should finally also be pointed out with regard to step S3, establishing the compensation information, that the use of a trained function, which implicitly realizes the comparison, is conceivable. For example, a CNN can be trained on the basis of the reference dataset 18 with different heights, from which training datasets are derived, wherein in its application, the projection data is transferred to the CNN and as output an optimized relative height is obtained as compensation information.

Returning to FIG. 1, in a step S4 there can be an application of the compensation information, since this describes the optimized relative height, which is also the deviation in height of the target region 3 described with respect to FIGS. 2 and 3. Thus the compensation information can be employed in the sense of compensation for a localization information relating to the target region, that for example already before the establishment of localization information a correcting height shift of the target region image dataset 21 by the optimized relative height takes place but a shift in the established localization information by the optimized relative height established as compensation information is undertaken.

In a step S5 the compensated localization information established in this way can be employed with regard to the height as a result of the bending of the couch under the patient 2, in particular for activation of the guidance facility 14, which acts at the intervention position as process position. For example laser markings for introducing a minimally-invasive instrument, for example a needle for a biopsy, and/or for a radiation therapy can be correctly visualized via the guidance facility and/or a controller of a process facility, in particular of a radiation facility and/or of a robot controlling the minimally invasive instrument, can also be controlled correctly and for high quality execution of the intervention on the basis of the corrected localization information.

Figure 7:
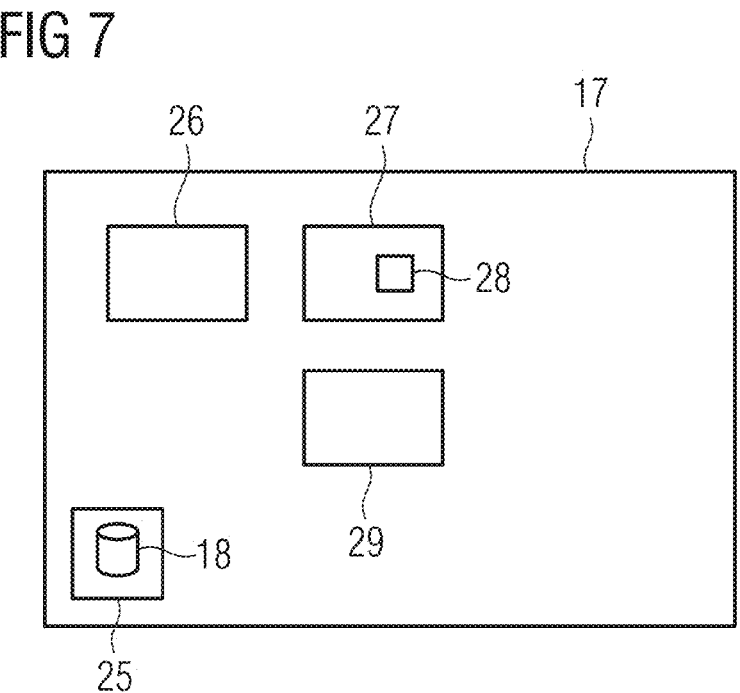
FIG. 7 shows a schematic representation of the functional structure of a control facility of the computed tomography facility according to one or more example embodiments.

FIG. 7 shows purely schematically the functional structure of the control facility 17. First of all, as already explained, this has a storage means 25, in which for example the reference dataset 18 can be stored, in particular together with the reference height setting. In a recording unit 26 of the control facility 17 the recording operation of the computed tomography facility 1 is controlled, in particular also the reference measurement of the step S1 and the recording of the target region image dataset 21 in accordance with step S2.

The control facility 17 further has a compensation information establishment unit 27 for establishing the compensation information in accordance with step S3 that, as subunits, can comprise a comparison subunit 28 and/or a reference dataset establishment unit (not shown here). In a compensation unit 29 the compensation can take place in accordance with step S4.

The control facility 17 can naturally also have further functional units, for example a localization information establishment unit for establishing the localization information and diverse activation units, for example also for carrying out the step S5.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although the invention has been illustrated and described in greater detail by one or more example embodiments, the invention is not restricted by the disclosed examples and other variations can be derived herefrom by the person skilled in the art, without departing from the scope of protection of the invention.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. A method for establishing compensation information to compensate for a bending of a couch of an object table of a computed tomography facility under a weight of an object to be recorded, wherein a target region image dataset of a target region of an examination object is recorded with the computed tomography facility at a recording position of the couch, the method comprising:

providing at least one marker visible in x-ray imaging at or in the couch;

providing a three-dimensional reference dataset of the marker for a non-loaded couch; and establishing the compensation information from a comparison between the reference dataset and the target region image dataset, the comparison taking place in a projection space, the comparison including establishing at least one comparison image with a recording geometry of an assigned projection image of the target region image dataset by forward projection from the reference dataset.

2. The method of claim 1, wherein the reference dataset is at least one of (i) established during an initial commissioning of the computed tomography facility with current couch characteristics or (ii) is provided from construction data of the object table.

3. The method of claim 2, wherein the reference dataset is based on a reference height setting being selected such that the at least one marker is acquired in each projection image of a reference measurement for the reference dataset, wherein the reference dataset is shifted by this deviation in a height direction.

4. The method of claim 1, wherein at least one elongated marker element at least one of extending in a direction of movement of the couch in parallel to an axis of rotation of an x-ray source of the computed tomography facility or corresponding to a longitudinal direction of the couch is used as the marker.

5. The method of claim 4, wherein at least one of at least one of the marker element extends at least one of over an entire length of the couch or the marker element is integrated into the couch, or at least one of at least three parallel marker elements are used adjacent thereto, and/or at different heights within the couch.

6. The method of claim 1, wherein the reference dataset is established showing only the at least one marker.

7. The method of claim 1, wherein, the comparison of the reference dataset with the target region image dataset includes, comparing the at least one comparison image with the assigned projection image for a number of projection images of the target region image dataset showing at least one of the at least one marker.

8. The method of claim 7, wherein the comparison images and the projection images are highpass filtered before the comparison using an identical filter.

9. The method of claim 1, further comprising:

establishing comparison images for different relative heights of the at least one marker from the reference dataset based on a recording geometry for the target region image dataset, and determining an optimized relative height with a highest match between a corresponding comparison image and target region image of the target region image dataset as compensation information.

10. The method of claim 9, further comprising:

selecting the optimized height in an optimization algorithm for maximization of a match described by at least one of a measure of similarity or a correlation.

11. The method of claim 1, wherein, the establishing includes, using a trained function using at least one part of the target region image dataset as input data, trained based on the reference dataset, to generate output data.

12. The method of claim 11, wherein, as training data for the function to be trained, training datasets, which comprise the reference dataset with at least one marker arranged at different relative heights, are created.

13. A computed tomography facility for use in processes related to a target region of an object comprising:

an object table with a couch for the object able to be moved in at least one direction, wherein at least one marker visible in x-ray imaging is provided on or in the couch; and a control facility, the control facility including, a storage, in which a three-dimensional reference dataset of the marker for a non-loaded couch is stored, a recording unit configured to record a target region image dataset showing the target region of the object at a recording position of the couch, a compensation information establishment unit configured to establish compensation information to compensate for a bending of the couch at the recording position under a weight of the object to be recorded, wherein the compensation information establishment unit has a comparison subunit configured to establish the compensation information from a comparison of the reference dataset with the target region image dataset, the comparison taking place in a projection space, the comparison including establishing at least one comparison image with a recording geometry of an assigned projection image of the target region image dataset by forward projection from the reference dataset, and a compensation facility configured to compensate for localization information relating to the target region.

14. A non-transitory computer-readable medium including instructions, when executed by a control facility of a computed tomography facility, cause the computed tomography facility to perform the method of claim 1.

15. A non-transitory computer-readable medium including instructions, when executed by a control facility of a computed tomography facility, cause the computed tomography facility to perform the method of claim 2.

16. The method of claim 3, wherein at least one elongated marker element at least one of extending in a direction of movement of the couch in parallel to an axis of rotation of an x-ray source of the computed tomography facility or corresponding to a longitudinal direction of the couch is used as the marker.

17. The method of claim 16, wherein at least one of at least one of the marker element extends at least one of over an entire length of the couch or the marker element is integrated into the couch, or at least one of at least three parallel marker elements are used adjacent thereto, and/or at different heights within the couch.

18. The method of claim 16, wherein the reference dataset is established showing only the at least one marker.

19. The method of claim 18, wherein, the comparison of the reference dataset with the target region image dataset includes, establishing at least one comparison image with a recording geometry of an assigned projection image of the target region image dataset by forward projection from the reference dataset, and comparing the at least one comparison image with the assigned projection image for a number of projection images of the target region image dataset showing at least one of the at least one marker.

20. The method of claim 19, wherein the comparison images and the projection images are highpass filtered before the comparison using an identical filter.

\* \* \* \* \*